(12) United States Patent
Nagy et al.

(10) Patent No.: US 12,173,124 B2
(45) Date of Patent: Dec. 24, 2024

(54) STYRENE-ASSISTED DEPOLYMERIZATION OF POLYOLEFINS

(71) Applicant: Basell Poliolefine Italia S.r.l., Milan (IT)

(72) Inventors: Sandor Nagy, Seabrook, TX (US); Daniel F. White, Houston, TX (US); Christopher D. Smith, Kingwood, TX (US); David L Ramage, Friendswood, TX (US)

(73) Assignee: Basell Poliolefine Italia S.r.l., Milan (IT)

( * ) Notice: Subject to any disclaimer, the term of this patent is extended or adjusted under 35 U.S.C. 154(b) by 631 days.

(21) Appl. No.: 17/450,234

(22) Filed: Oct. 7, 2021

(65) Prior Publication Data
US 2022/0112352 A1    Apr. 14, 2022

Related U.S. Application Data

(60) Provisional application No. 63/089,706, filed on Oct. 9, 2020.

(51) Int. Cl.
*C08J 11/20*    (2006.01)

(52) U.S. Cl.
CPC ............ *C08J 11/20* (2013.01); *C08J 2323/06* (2013.01); *C08J 2323/12* (2013.01); *C08J 2325/06* (2013.01)

(58) Field of Classification Search
USPC ........................................................ 521/47
See application file for complete search history.

(56) References Cited

U.S. PATENT DOCUMENTS

| | | |
|---|---|---|
| 2020/0392319 A1 | 12/2020 | Di Mondo et al. |
| 2021/0277202 A1 | 9/2021 | Wilhelmus et al. |

FOREIGN PATENT DOCUMENTS

| | | | |
|---|---|---|---|
| WO | WO-2012061236 A2 * | 5/2012 | ............ B01J 8/062 |
| WO | 2018224482 A1 | 12/2018 | |
| WO | 2019195915 A1 | 10/2019 | |

OTHER PUBLICATIONS

Miskolczi et al.; Thermal Degradation of Polyethylene and Polystyrene from the Packaging Industry over Different Catalysts into Fuel-Like Feed Stocks, Polymer Degradation and Stability Barking, GB, vol. 91, No. 3, Mar. 1, 2006, pp. 517-526, XP027949441, ISSN: 0141-3910.
The International Search Report and The Written Opinion for PCT/IB2021/000704 mailed Feb. 24, 2022.

* cited by examiner

*Primary Examiner* — Terressa Boykin

(57) ABSTRACT

Methods of depolymerizing polyolefin-based material into useful petrochemical products using styrene oligomers or polymers, and heat are described. The styrene oligomers or polymers improve the depolymerization reaction by decreasing the halftime for the depolymerization, which results in a higher depolymerization rate and a shorter residence time in the depolymerization unit, allowing for a predictable depolymerization reaction, and decreasing the branching or aromatic formations in the product.

12 Claims, No Drawings

STYRENE-ASSISTED DEPOLYMERIZATION OF POLYOLEFINS

PRIOR RELATED APPLICATIONS

This application claims the benefit of priority to U.S. Provisional Patent Application No. 63/089,706, filed on Oct. 9, 2020, which is incorporated herein by reference in its entirely.

FEDERALLY SPONSORED RESEARCH STATEMENT

Not applicable.

REFERENCE TO MICROFICHE APPENDIX

Not applicable.

FIELD OF THE DISCLOSURE

The disclosure relates to methods of depolymerizing polyolefin-based material using styrene oligomers or polymers and heat to form useful petrochemical products.

BACKGROUND OF THE DISCLOSURE

Heightened standards of living and increased urbanization have led to an increased demand for polymer products, particularly polyolefin plastics. Polyolefins have been frequently used in commercial plastics applications because of their outstanding performance and cost characteristics. Polyethylene (PE), for example, has become one of the most widely used and recognized polyolefins because it is strong, extremely tough, and very durable. This allows for it to be highly engineered for a variety of applications. Similarly, polypropylene (PP) is mechanically rugged yet flexible, is heat resistant, and is resistant to many chemical solvents like bases and acids. Thus, it is ideal for various end-use industries, mainly for packaging and labeling, textiles, plastic parts and reusable containers of various types.

The downside to the demand for polyolefin plastics is the increase in waste. Post-consumer plastic waste typically ends up in landfills, with about 12% being incinerated and about 9% being diverted to recycling. In landfills, most plastics do not degrade quickly, becoming a major source of waste that overburdens the landfill. Incineration is also not an ideal solution to treating the plastic wastes as incineration leads to the formation of carbon dioxide and other greenhouse gas emissions. As such, there has been much interest in developing methods of recycling plastic waste to reduce the burden on landfills while being environmentally friendly.

A drawback to the recycling of plastic wastes is the difficulty in successfully producing commercially usable or desirable products. Plastic waste recycling currently includes washing the material and mechanically reprocessing it; however, the resulting pellets remain contaminated with impurities such as food residue, dyes, and perfume. These impurities render the pellets undesirable for most uses based on both performance and appearance.

Recent advances have focused on converting plastic waste to useable products like fuel sources or commercially important raw material. Methods of performing pyrolysis of the plastic waste stream followed by catalytic depolymerization have been developed to generate various products: gases, gasoline fractions, kerosene fractions, diesel fractions and waxes.

Unfortunately, these processes are costly and time-consuming because they require a lot of energy to fully decompose polyolefin wastes to useful classes of products. Further, the reaction products themselves are unpredictable due to secondary reactions occurring under pyrolysis conditions, resulting in the formation of branched and aromatic products. The catalysts themselves also tend to be easily poisoned by impurities in the polymer feed.

Despite the advances made in recycling polymers, there is a continued need for the development of a robust process for the conversion of plastics to useful petrochemical products that minimizes formation of branched and/or aromatics products.

SUMMARY OF THE DISCLOSURE

The present disclosure provides improved methods for thermally depolymerizing polyolefin-based material. The improved methods rely on thermally depolymerizing a feed stream with one or more polyolefins in the presence of styrene oligomers or polymers. Specifically, styrene oligomers or polymers, such as oligostyrene and polystyrene, are mixed with a polyolefin-based material in a depolymerization unit and heated in the absence of oxygen. The styrene oligomers or polymers initiates a radical depolymerization reaction that can proceed at a faster depolymerization rate (smaller depolymerization half time of reaction) than depolymerization reactions of the polyolefin-based material without the styrene oligomers or polymers. This radical depolymerization results in the formation of liquid products with minimal branching or aromatic formation. The liquid products can then be used as is, or undergo further processing such as olefins crackers, to improve the feedstock.

The methods described herein can be used to treat any polyolefin-based material, including post-industrial waste and post-consumer use. Treatment of post-consumer polyolefin waste is of particular importance due to the overburdening of landfills and the potential to generate raw materials from the wastes. The methods described here relate to the processing of post-consumer waste after it has been sorted by the processing center at a landfill, or other recycling center, to separate polyolefin-based materials from other recyclable materials such as glass, cellulose (paper), polyvinyl polymers, and the like.

The present disclosure includes any of the following embodiments in any combination(s):

A method of depolymerizing polyolefins comprising adding a polyolefin-based feed stream and a styrene oligomer or a styrene polymer to a depolymerization unit heated to a predetermined temperature; and reacting the polyolefin-based feed stream with the styrene oligomer or the styrene polymer to depolymerize the polyolefin-based feed stream.

A method of depolymerizing polyolefins comprising adding a polyolefin-based feed stream and a styrene oligomer to a depolymerization unit heated to a predetermined temperature; and reacting the polyolefin-based feed stream with the styrene oligomer to depolymerize the polyolefin-based feed stream.

A method of depolymerizing polyolefins comprising adding a polyolefin-based feed stream and a styrene polymer to a depolymerization unit heated to a predetermined temperature; and reacting the polyolefin-based feed stream with the styrene polymer to depolymerize the polyolefin-based feed stream.

Any of the herein described methods, wherein the rate of depolymerization of the polyolefin-based feed stream is at least 10% higher than the rate of depolymerization for the polyolefin-based feed stream without the styrene oligomer or the styrene polymer.

Any of the herein described methods, wherein an onset temperature of depolymerization for the polyolefin-based feed stream is 5% less than the onset temperature of the polyolefin-based feed stream without the styrene oligomer or the styrene polymer Any of the herein described methods, wherein the half time of depolymerization of the polyolefin-based feed stream is at least 30% lower than the half time of depolymerization for the polyolefin-based feed stream without the styrene oligomer or the styrene polymer.

Any of the herein described methods, wherein the styrene oligomer is oligostyrene.

Any of the herein described methods, wherein the styrene polymer is polystyrene.

Any of the herein described methods, wherein the styrene oligomers and polymers have an average molecular weight between 500 Da and 20 kDa.

Any of the herein described methods, wherein the polyolefin-based feed stream is a low-density polyethylene, a high density polyethylene, a polypropylene, or a combination thereof.

Any of the herein described methods, wherein the polyolefin-based feed stream is post-consumer waste.

Any of the herein described methods, wherein the polyolefin-based feed stream is post-industrial waste.

Any of the herein described methods, wherein the polyolefin-based feed stream comprises both post-industrial waste and post-consumer waste.

Any of the herein described methods, wherein the styrene polymer is post-consumer waste, post-industrial waste, or a combination thereof.

Any of the herein described methods, wherein the styrene oligomer is post-consumer waste, post-industrial waste, or a combination thereof.

Any of the herein described methods, wherein the concentration of the styrene oligomer or the styrene polymer is between greater than 0 to about 20 weight percent.

Any of the herein described methods, wherein the concentration of the styrene oligomer or the styrene polymer is between about 2.5 and about 5 weight percent.

Any of the herein described methods, wherein the predetermined temperature is between about 200° C. and about 600° C.

A method of depolymerizing polyolefins comprising adding a polyolefin-based feed stream and a styrene oligomer or a styrene polymer to a depolymerization unit heated to a temperature between about 200° C. and about 600° C.; and reacting the polyolefin-based feed stream with the styrene oligomer or the styrene polymer to depolymerize the polyolefin-based feed stream. In some embodiments, the rate of depolymerization of the polyolefin-based feed stream is at least 10% higher than the rate of depolymerization for the polyolefin-based feed stream without the styrene oligomer or the styrene polymer. Additionally, or as an alternative, the onset temperature of depolymerization for the polyolefin-based feed stream is 5% less than the onset temperature of the polyolefin-based feed stream without the styrene oligomer or the styrene polymer.

This summary is provided to introduce a selection of concepts that are further described below in the detailed description. This summary is not intended to identify key or essential features of the claimed subject matter, nor is it intended to be used as an aid in limiting the scope of the claimed subject matter.

DEFINITIONS

As used herein, the terms "depolymerization half time" or "half time of depolymerization" refer to the time needed to achieve a 50% loss of mass of a sample at a specific temperature during a TGA thermolysis reactions.

As used herein, "residence time" refers to the time needed to depolymerize a batch of polymer waste in a depolymerization unit.

As used herein, "thermolysis" refers to a thermal depolymerization reaction occurring in the absence of oxygen.

As used herein, "post-consumer waste" refers to a type of waste produced by the end consumer of a material stream.

As used herein, "post-industrial waste" refers to a type of waste produced during the production process of a product.

All concentrations herein are by weight percent ("wt %") unless otherwise specified.

As used herein, "oligomer" refers to a molecule that consists of a few ($\leq$100) repeat units. As used herein, "polymer" refers to a molecule that consists of many (>100) repeat units. Both oligomers and polymers can be synthesized from one or more monomers.

The term "oligostyrene" refers to an oligomer comprising repeat units derived from a styrene monomer only. The term "polystyrene" refers to a polymer comprising repeat units derived from a styrene monomer only.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| EPS | Expandable polystyrene |
| GC | Gas Chromatography |
| GPC | Gel Permeation Chromatography |
| HDPE | High density polyethylene |
| PE | polyethylene |
| PP | polypropylene |
| PS | Polystyrene |
| TGA | Thermogravimetric Gravimetric Analysis |
| wt % | weight percent |

DESCRIPTION OF EMBODIMENTS OF THE DISCLOSURE

The present disclosure provides improved methods for recycling polyolefin-based materials into commercially important raw material using styrene oligomers or polymers. Specifically, styrene oligomers or polymers are mixed with a polyolefin-based feed stream comprising at least one polyolefin-based material in a depolymerization unit. Upon heating this mixture, a thermolysis reaction occurs, wherein the styrene oligomers or polymers initiate the depolymerization of the polyolefin-based material to generate a usable liquid product with minimal branching or aromatics formation.

There are many advantages of using styrene oligomers or polymers to improve the thermal depolymerization of the polyolefins. As mentioned above, the styrene oligomers or polymers are not a catalyst for the recycling process. Rather, they act as an initiator. In more detail, the double bond (C=C) in the backbone of the styrene oligomer or polymer undergoes a homolytic breaking at low temperatures, resulting in a radical that is stabilized by the aromatic ring. This radical then initiates a chain reaction with the polyolefin, facilitating a radical depolymerization of the polyolefin in the feed stream. This limits isomerization reactions during depolymerization, resulting in a simpler mix of reaction products that are similar to the products from the same feed stream depolymerized without a styrene oligomer and polymer. Thus, the reaction products for a given polymer feed stream composition are easily predictable.

Another advantage of using styrene oligomers and polymers is that they are readily available in post-consumer and post-industrial wastes, particular in the form of expanded polystyrene foam (EPS). For the past 15 years, the worldwide EPS industry has managed to recycle an average of 19% of post-consumer and 25% of post-industrial EPS, with the remaining waste being buried in landfills. The present methods allow for easy combination of polystyrene destined for landfills with post-consumer and post-industrial polyolefin waste. As an example, polyolefin-based materials separated by the processing center at a landfill, or other recycling center, can be combined with foamed polystyrene cups and other polystyrene food containers in the depolymerization unit. Thus, not only are the polyolefin-based materials being depolymerized and recycled, but less polystyrene foam will be placed in landfills. Alternatively, 'new' polystyrenes, or other styrene oligomers and polymers, can be produced specifically for use in the present methods.

Finally, styrene oligomers and polymers are robust in that they are less likely to be affected by 'poisons' in the polymer feed stream than other traditional depolymerization catalysts. This allows for a wider range of polyolefin feed compositions than other depolymerization methods.

A wide weight range of added styrene oligomers and polymers can improve the depolymerization rate of polyolefins. In some embodiments, the styrene oligomers and polymers are present in a concentration of greater than 0 to about 50 wt % of the feed stream. Alternatively, the styrene oligomers and polymers are present in a concentration of between greater than 0 to about 30 wt %, between about 2.5 to about 10 wt %, between about 5 to about 20 wt %, between about 15 to about 30 wt %, between about 25 to about 50 wt %, or between about 35 to about 50 wt %. In yet other embodiments, the styrene oligomers and polymers are present in a concentration of 2.5, 5, 10, 15, or 20 wt %.

The styrene oligomers and polymers can have an average molecular weight between 500 Da and 20 kDa. In some embodiments, the added styrene component has only styrene repeat units, such as oligostyrene and polystyrene. In some embodiments, the added styrene component has one or more other repeat units besides styrene. In other embodiments, the added styrene component is an oligostyrene with 10 to about 80 repeat units; alternatively, the oligostyrene has 10 to about 50 repeat units; alternatively, the oligostyrene has 40 to about 80 repeat units.

The presently described methods can be applied to a feed stream comprising material with a single polyolefin component, or a mixture of polyolefin components in any amount. A broad range of polyolefins can be present in the feed stream, including but not limited to, polyethylene (both high and low density), polypropylene, ethylene-propylene copolymers, polybutene-1, polyisobutene, and copolymers thereof. Further, the waste is not limited to any particular form so films, foams, textiles or other shaped material can be treated with the described methods. The feed can contain post-consumer polyolefin waste, post-industrial polyolefin wastes, or both post-industrial and post-consumer polyolefin waste.

The polyolefin-based material, combined with the styrene oligomer and polymer, are treated in depolymerization units with operating temperatures between about 200 and about 600° C. Alternatively, the operating temperature of the depolymerization unit is between about 225 and about 500° C. In yet another alternative, the operating temperature of the depolymerization unit is between about 250 and about 450° C., or about 400° C.

The polyolefin feed stream is treated in batches in the depolymerization unit due to the residence time needed to fully depolymerize the stream. The estimated residence time for each batch will be between about 30 to about 180 minutes, depending on the heat transferability of the depolymerization unit and the amount of the styrene oligomer or polymer. Alternatively, the estimated residence time is about 60 minutes.

Under the above reaction conditions, batches with even small amounts of styrene oligomers and polymers (less than 5 wt %) are expected to have a half time of depolymerization that is at least 30% lower than polyolefin batches without the added styrene oligomers and polymers. In some embodiments, the half time of depolymerization is reduced by at least 40%. For larger amounts of styrene oligomers and polymers (about 10 to about 20 wt %), the half time of depolymerization is reduced by at least 59%, depending on the polyolefin content.

Thus, the presently disclosed depolymerization methods allow for a quicker depolymerization of polyolefin-based materials into predictable liquid products with minimal branching or aromatic formation. The liquid products can then be used as is or further treated to improve the quality of the product stream. Additionally, the methods reduce the amount styrene oligomer and polymers waste in landfills.

EXAMPLES

The following examples are included to demonstrate embodiments of the appended claims using the above described methods of depolymerizing polyolefins. These examples are intended to be illustrative only, and not to unduly limit the scope of the appended claims. Those of skill in the art should appreciate that many changes can be made in the specific embodiments which are disclosed and still obtain a like or similar result without departing from the spirit and scope of the disclosure herein. In no way should the following examples be read to limit, or to define, the scope of the appended claims.

TGA DEPOLYMERIZATION

A series of single component polyolefin feed streams were processed using Thermogravimetric Analysis (TGA) as a depolymerization unit to investigate the effect of polystyrene as a depolymerization initiator. The feed consisted of either a high density polyethylene (grade ACP9255, a Lyondell-Basell product) or polypropylene (grade Moplen HP522H, a LyondellBasell product). Uniform samples were prepared by combining 10 g of the polyolefin feed melt-compounded with various amounts of polystyrene (PS 3010-01, Sigma-Aldrich) in a HAAK MiniCTW compounder at 200° C. and 200 RPM for 5 minutes.

For the TGA thermolysis reactions, the prepared samples were heated under nitrogen at 10K/min to the desired depolymerization temperature in a Mettler Toledo TGA/DSC 3+ (Mettler Toledo, Columbus, Ohio) and held for 1 hour. For these examples, a depolymerization temperature of 400° C. was used. The depolymerization half time at a specific temperature, defined as the time needed to achieve a 50% loss of mass, was recorded directly if the value was less than 60 minutes, or determined under the assumption of first order decomposition kinetics as $t_{1/2}=0.693/k$, where k is the first order rate constant determined graphically using a $Ln(C_0/C)$ vs time plot if the value was greater than 60 minutes.

The depolymerization half time is relative to the residence time needed in a large scale depolymerization unit. The shorter the half time, the shorter the residence time for a batch of a polymer feed in a depolymerization unit, and the higher the depolymerization rate.

The catalytic effect of polystyrene on HDPE is shown Table 1. Comparative Example 1 was depolymerized without polystyrene. The depolymerization half time for Comp. Ex. 1 was 347 minutes at 400° C. The addition of polystyrene reduced the half time for this HDPE feed. Even at lower concentrations of polystyrene (≤5%), large reductions in the depolymerization half time are seen. A 40% reduction in the half time was seen with a polystyrene concentration as low as 2.5%. At a concentration of 20% of polystyrene, the half time decreased by about 82%. This shows that even a small amount of added polystyrene can reduce the residence time needed to fully depolymerize HDPE into usable petrochemical products.

TABLE 1

Results from TGA depolymerization of HDPE with polystyrene

| | Concentration of Polystyrene (%) | K at 400° C. | Half Time (min) | Half Time reduction |
|---|---|---|---|---|
| Comparative Example 1 | 0 | 0.002 | 347 | n/a |
| Example 1 | 2.5 | 0.0034 | 204 | 41.2% |
| Example 2 | 5 | 0.0051 | 136 | 60.8% |
| Example 3 | 10 | 0.0078 | 89 | 74.4% |
| Example 4 | 20 | 0.011 | 63 | 81.8% |

Similar decreases in the depolymerization half time (with corresponding increases in the depolymerization rate) are seen when the polyolefin was changed to PP. As shown in Table 2, large reductions in the depolymerization half time for PP were seen, even with lower concentrations of polystyrene (≤5%). At a concentration of 20% of polystyrene, the depolymerization half time decreased by about 62%. Though this is lower than the reduction observed with the HDPE stream, the reduction in half time of the PP stream with 20 wt % polystyrene is still more rapid than Comparative Example 2.

TABLE 2

Results from TGA depolymerization of PP with polystyrene

| | Concentration of Polystyrene (%) | K at 400° C. | Half Time (min) | Half Time reduction |
|---|---|---|---|---|
| Comparative Example 2 | 0 | 0.0158 | 44 | n/a |
| Example 6 | 2.5 | 0.0308 | 23 | 47.7% |
| Example 7 | 5 | 0.0353 | 20 | 54.5% |
| Example 8 | 10 | 0.0387 | 18 | 59.1% |
| Example 9 | 20 | 0.0404 | 17 | 61.4% |

Polystyrene was able to demonstrate an improvement on the depolymerization rate from a concentration of 2.5 to 20% for a variety of polyolefins, which translates to less time being needed for depolymerization of these compounds in a larger scaled reactor.

Concentrations above 20% polystyrene also reduced the depolymerization rate of HDPE and PP. However, this benefit may be offset by the creation of more aromatic products, namely styrene, in the resulting reaction product. The presence of aromatic products affects the quality of the resulting feedstock. As such, additional steps to hydrogenate the reaction products may be necessary depending on the end use of the reaction products.

Although the examples are described using polystyrene, other styrene polymers can be used. Additionally, styrene oligomers having a few repeat units up to 100 repeat units, such as oligostyrene, will also be able to reduce the depolymerization rate of polyolefin feeds.

The presently described methods of using a styrene oligomer or polymer for the depolymerization of polyolefins streams can provide a lower energy efficiency (i.e. more cost effective) when compared to methods without the use of a styrene oligomer or polymer.

The invention claimed is:

1. A method of depolymerizing polyolefins comprising:
   a) adding a polyolefin-based feed stream and a styrene oligomer or a styrene polymer to a depolymerization unit heated to a temperature between about 200° C. and about 600° C.; and
   b) reacting said polyolefin-based feed stream with said styrene oligomer or said styrene polymer to depolymerize said polyolefin-based feed stream.

2. The method of claim 1, wherein said polyolefin-based feed stream is combined with said styrene oligomer.

3. The method of claim 2, wherein said styrene oligomer is an oligostyrene.

4. The method of claim 1, wherein said polyolefin-based feed stream is combined with said styrene polymer.

5. The method of claim 4, wherein said styrene polymer is a polystyrene.

6. The method of claim 1, wherein said polyolefin-based feed stream is a low-density polyethylene, a high density polyethylene, a polypropylene, or a combination thereof.

7. The method of claim 1, wherein said polyolefin-based feed stream is post-consumer waste.

8. The method of claim 1, wherein said polyolefin-based feed stream is post-industrial waste.

9. The method of claim 1, wherein said polyolefin-based feed stream comprises both post-industrial waste and post-consumer waste.

10. The method of claim 1, wherein the polystyrene is post-consumer waste, post-industrial waste, or a combination thereof.

11. The method of claim 1, wherein the concentration of said styrene oligomer or said styrene polymer is between greater than 0 to about 20 weight percent.

12. The method of claim 11, wherein the concentration of said styrene oligomer or said styrene polymer is between about 2.5 and about 5 weight percent.

* * * * *